US009384947B2

(12) United States Patent
Watson et al.

(10) Patent No.: US 9,384,947 B2
(45) Date of Patent: Jul. 5, 2016

(54) COLD PLASMA TREATMENT DEVICES AND ASSOCIATED METHODS

(75) Inventors: Gregory A. Watson, Sanford, FL (US); Robert M. Hummel, Cave Creek, AZ (US); Marc C. Jacofsky, Phoenix, AZ (US); David J. Jacofsky, Peoria, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 712 days.

(21) Appl. No.: 13/620,092

(22) Filed: Sep. 14, 2012

(65) Prior Publication Data
US 2013/0072858 A1 Mar. 21, 2013

Related U.S. Application Data

(60) Provisional application No. 61/535,250, filed on Sep. 15, 2011.

(51) Int. Cl.
*H01J 7/24* (2006.01)
*H01J 37/32* (2006.01)
(Continued)

(52) U.S. Cl.
CPC ............. *H01J 37/321* (2013.01); *A61L 2/00* (2013.01); *A61L 2/0094* (2013.01); *A61L 2/14* (2013.01); *A61M 15/02* (2013.01); *A61M 16/06* (2013.01); *A61M 16/12* (2013.01); *A61N 1/40* (2013.01); *A61N 1/44* (2013.01); *H01J 37/3244* (2013.01); *H01J 37/3266* (2013.01); *H01J 37/32348* (2013.01); *H05H 1/2406* (2013.01); *H05H 1/46* (2013.01); *A61M 2202/025* (2013.01); *A61M 2202/0208* (2013.01); *H05H 2001/2412* (2013.01); *H05H 2001/466* (2013.01);
(Continued)

(58) Field of Classification Search
None
See application file for complete search history.

(56) References Cited

U.S. PATENT DOCUMENTS

| 2,927,322 A | 3/1960 | Simon et al. |
| 3,432,722 A | 3/1969 | Naydan et al. |

(Continued)

FOREIGN PATENT DOCUMENTS

| JP | 2006-244938 | 9/2006 |
| WO | WO 96/00108 | 1/1996 |

(Continued)

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.
(Continued)

*Primary Examiner* — Douglas W Owens
*Assistant Examiner* — Srinivas Sathiraju
(74) *Attorney, Agent, or Firm* — Sterne, Kessler, Goldstein & Fox P.L.L.C.

(57) ABSTRACT

A cold plasma mask application device for delivery of a cold plasma to the face of a patient. An appropriate gas is introduced into a gas containment area that is energized by one or more electrodes that receive energy from a pulsed source. The plasma can be prevented from contact with the patient's face, or can be allowed to make contact with the patient's face at the appropriate treatment area. A three-layer approach to the manufacture of the cold plasma mask application device is also described. Such a device and method can be used to treat acne as well as complex facial wounds such as those resulting from trauma, melanoma, and other cancers of the face, rosacea, and psoriasis.

22 Claims, 13 Drawing Sheets

(51) Int. Cl.
*A61M 16/06* (2006.01)
*A61M 16/12* (2006.01)
*A61M 15/02* (2006.01)
*A61N 1/44* (2006.01)
*H05H 1/24* (2006.01)
*A61N 1/40* (2006.01)
*A61L 2/00* (2006.01)
*H05H 1/46* (2006.01)
*A61L 2/14* (2006.01)

(52) U.S. Cl.
CPC .... *H05H2001/4682* (2013.01); *H05H 2240/20* (2013.01); *H05H 2245/1225* (2013.01); *H05H 2277/10* (2013.01)

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,381,789 A | 1/1995 | Marquardt | |
| 5,643,336 A * | 7/1997 | Lopez-Claros | 607/104 |
| 5,698,164 A | 12/1997 | Kishioka et al. | |
| 5,724,964 A * | 3/1998 | Brunson et al. | 128/206.19 |
| 5,765,556 A * | 6/1998 | Brunson | 128/206.19 |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A * | 10/1999 | Selwyn | 156/345.39 |
| 5,977,715 A | 11/1999 | Li et al. | |
| 6,029,269 A * | 2/2000 | El-Soudani | 2/2.5 |
| 6,055,982 A * | 5/2000 | Brunson et al. | 128/206.12 |
| 6,096,564 A | 8/2000 | Denes et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,419,487 B2 * | 9/2008 | Johnson et al. | 606/41 |
| 7,494,488 B2 * | 2/2009 | Weber | 606/2 |
| 7,608,839 B2 | 10/2009 | Coulombe et al. | |
| 7,633,231 B2 * | 12/2009 | Watson | 315/111.51 |
| 7,658,891 B1 * | 2/2010 | Barnes | 422/186.03 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 7,930,772 B2 * | 4/2011 | Fontanez | 2/425 |
| 8,267,884 B1 * | 9/2012 | Hicks | 604/23 |
| 8,294,369 B1 | 10/2012 | Laroussi | |
| 8,460,283 B1 | 6/2013 | Laroussi et al. | |
| 2002/0129902 A1 | 9/2002 | Babayan et al. | |
| 2003/0222586 A1 | 12/2003 | Brooks et al. | |
| 2005/0088101 A1 | 4/2005 | Glidden et al. | |
| 2005/0179395 A1 | 8/2005 | Pai | |
| 2006/0156983 A1 * | 7/2006 | Penelon et al. | 118/723 E |
| 2006/0182704 A1 * | 8/2006 | Gianelli | 424/70.14 |
| 2006/0189976 A1 | 8/2006 | Karni et al. | |
| 2008/0145553 A1 | 6/2008 | Boulos et al. | |
| 2008/0159925 A1 | 7/2008 | Shimizu et al. | |
| 2009/0188626 A1 | 7/2009 | Lu et al. | |
| 2010/0133979 A1 | 6/2010 | Lu | |
| 2010/0145260 A1 * | 6/2010 | Watson | 604/23 |
| 2010/0191314 A1 * | 7/2010 | Young | 607/109 |
| 2011/0022043 A1 * | 1/2011 | Wandke et al. | 606/41 |
| 2011/0042560 A1 | 2/2011 | Ouyang et al. | |
| 2012/0100524 A1 | 4/2012 | Fridman et al. | |
| 2012/0187841 A1 * | 7/2012 | Kindel et al. | 315/111.21 |
| 2012/0259270 A1 * | 10/2012 | Wandke et al. | 604/23 |
| 2013/0022514 A1 | 1/2013 | Morfill et al. | |
| 2013/0052092 A1 * | 2/2013 | Yang et al. | 422/162 |
| 2013/0053762 A1 | 2/2013 | Rontal et al. | |
| 2013/0072858 A1 * | 3/2013 | Watson et al. | 604/23 |
| 2013/0134878 A1 | 5/2013 | Selwyn | |
| 2013/0199540 A1 * | 8/2013 | Buske | 128/845 |
| 2014/0000810 A1 | 1/2014 | Franklin et al. | |
| 2014/0178604 A1 * | 6/2014 | Selwyn | 427/562 |
| 2015/0209174 A1 * | 7/2015 | Abreu | |

FOREIGN PATENT DOCUMENTS

| | | |
|---|---|---|
| WO | WO 00/78388 A1 | 12/2000 |
| WO | WO 2005/084569 A1 | 9/2005 |
| WO | WO 2006/116252 | 11/2006 |
| WO | WO 2007/063186 A1 | 6/2007 |
| WO | WO 2007/124910 A2 | 11/2007 |
| WO | WO 2010.107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http//www.physorg.com/printnews.php?newsid-6688>.

Book of Abstracts 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, WILEY-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

Fridman et al., "Comparison of Direct and Indirect Effects of Non-Thermal Atmospheric-Pressure Plasma on Bacteria," *Plasma Processl Polym.*, 4, 370-375, 6 pages, WILEY-VCH Verlag GmbH & Co. KGaA, Weinheim (2007).

(56) References Cited

OTHER PUBLICATIONS

Alexander Fridman, "Plasma Chemistry," pp. 263-271, Cambridge University Press, 2008, 9 pages.
O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).
Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).
Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).
Walsh et al., "Three distinct modes in a cold atmospheric pressure plasma jet," *J. Phys. D.: Appl. Phys.* 43 075201, 14 pages, IOP Publishing Ltd (Feb. 3, 2010).
Ricci et al., "The effect of stochastic electrical noise on hard-to-heal wounds," *Journal of Wound Care*, 8 pages, 19:3 Mark Allen Publishing Ltd (Mar. 2010).
U.S. Appl. No. 61/485,747, filed May 13, 2011, inventor Thomas J. Sheperak, 14 pages.
Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).
Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages., IOP Publishing Ltd (Apr. 4, 2012).
Walsh et al., "Chaos in atmospheric-pressure plasma jets," *Plasma Sources Sci. Technol.*, 21 034008, 8 pages, IOP Publishing Ltd (May 2, 2012).
Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).
Dobrynin, et al., "Live Pig Skin Tissue and Wound Toxicity of Cold Plasma Treatment," *Plasma Medicine*, 1(1):93-108, 16 pages, Begell House, Inc. (2011).
Fernández, et al., "The inactivation of *Salmonella* by cold atmosphere plasma treatment," *Food Research International*, 45:2, 678-684, 7 pages, Elsevier Ltd. (Mar. 2012).
Tien, et al., "The Bilayer Lipid Membrane (BLM) Under Electrical Fields," *IEEE Transactions on Dielectrics and Electrical Institute*, 10:5, 717-727, 11 pages (Oct. 2003).

Jayaram, et al.., "Optimization of Electroporation Waveforms for Cell Sterilization," *IEEE Transactions on Industry Applications*, 40:6, 1489-1497, 9 pages (2004).
Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).
Fridman, et al., "Use of Non-Thermal Atmospheric Pressure Plasma Discharge for Coagulation and Sterilization of Surface Wounds," 6 pages (Jun. 2005).
Fridman, et al., "Blood Coagulation and Living Tissue Sterilization by Floating-Electrode Dielectric Barrier Discharge in Air," *Plasma Chem Plasma Process*, 26(4): 425-442, 18 pages, Springer Science Business Media, Inc. (2006).
Gurol, et al., "Low Temperature Plasma for decontamination of *E. coli* in milk," *International Journal of Food Microbiology*, 157: 1-5, 5 pages, Elsevier B.V. (Jun. 2012).
Lado, et al., "Alternative food-preservation technologies: efficacy and mechanisms," *Microbes and Infection*, 4: 433-440 8 pages, Elsevier SAS (2002).
Leduc, et al., "Cell permeabilization using a non-thermal plasma," *New Journal of Physics*, 11: 115021, 12 pages, IOP Publishing Ltd and Deutsche Physikalische Gesellschaft (2009).
Machado, et al., "Moderate electric fields can inactivate *Escherichia coli* at room temperature," *Journal of Food Engineering*, 96: 520-527, 8 pages, Elsevier Ltd. (2009).
Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).
Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).
Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).
Toepfl, et al., "High intensity pulsed electric fields applied for food preservation," *Chemical Engineering and Processing*, 46: 537-546, 10 pages, Elsevier B.V. (2007).
International Search Report mailed Nov. 29, 2012 for Appl. No. PCT/US2012/55599, 3 pages.
Written Opinion of International Searching Authority mailed Nov. 29, 2012 for Appl. No. PCT/US2012/55599, 4 pages.
English-language abstract for: Ryuichiro et al. JP-2006-244938, Sep. 14, 2006 (listed as FP3), 2 pages.
The extended European Search Report mailed Feb. 5, 2015 for Appl. No. EP 12 83 2526, 8 pages.

* cited by examiner

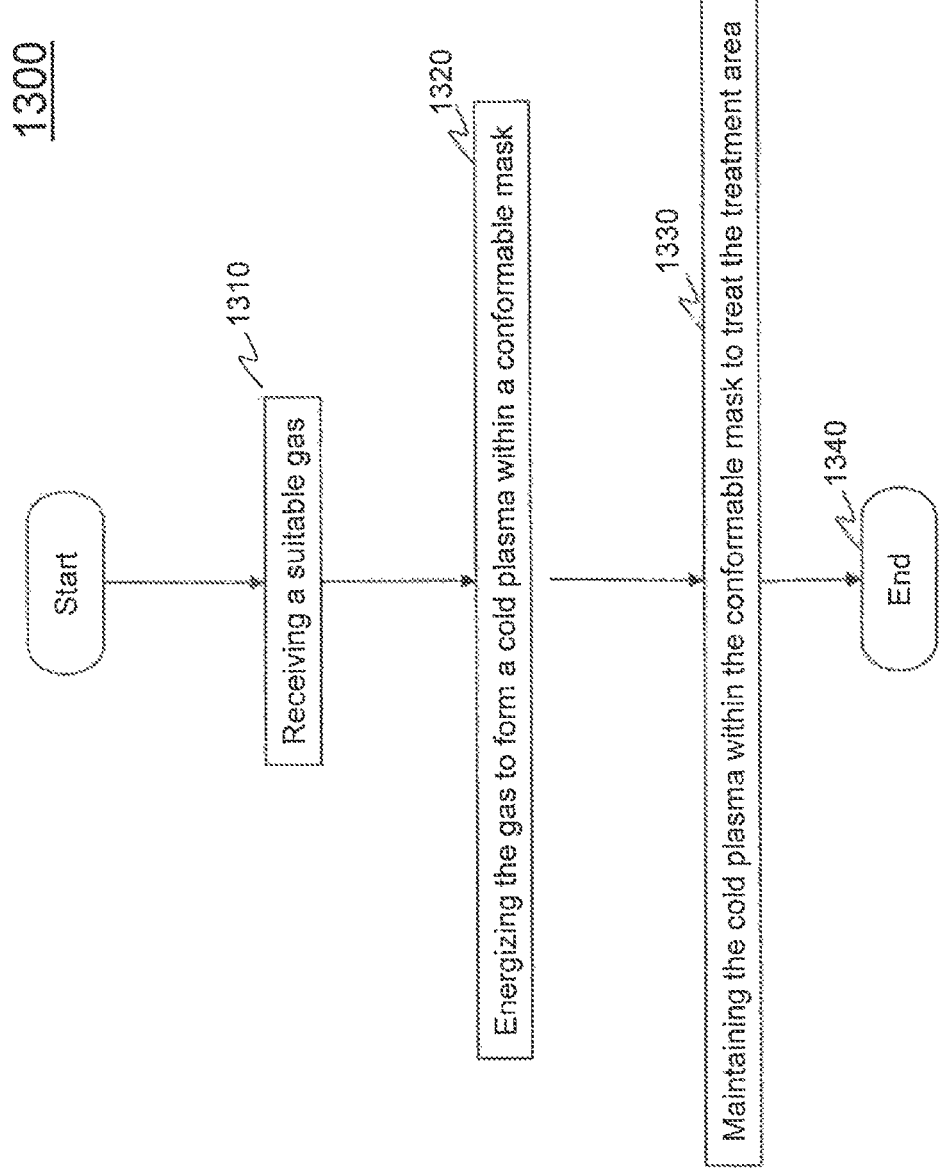

COLD PLASMA TREATMENT DEVICES AND ASSOCIATED METHODS

CROSS REFERENCE TO RELATED APPLICATIONS

The present application claims the benefit under 35 U.S.C. §119(e) of U.S. Provisional Patent Application No. 61/535,250, entitled "Harmonic Cold Plasma Devices and Associated Methods", filed on Sep. 15, 2011, which is hereby expressly incorporated by reference in its entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

1. Field of the Art

The present invention relates to devices and methods for creating cold plasmas, and, more particularly, to cold plasma treatment methods and application devices.

2. Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Different applications of cold plasma devices require different size cold plasma plumes and different dimensional devices to produce those cold plasma plumes. For example, some medical treatments require a large cold plasma plume to treat a large external wound, while other treatments require a small cold plasma device that can be coupled to an elongated medical device that can traverse a small body passageway to reach a small internal treatment site.

Acne is a large problem for many people. It affects children, teens, and adults. There is a multimillion dollar industry surrounding the prevention and treatment of acne. Acne is caused by bacteria in the pores and subcutaneous glands of the skin. Powerful antibiotics have been used both systemically and topically to control these bacteria, as well as benzoyl peroxide, witch hazel, and other astringents to clean pores and sanitize the skin surface. There are also mechanical devices that claim to physically clean pores and debride the skin surface.

BRIEF SUMMARY OF THE INVENTION

Cold plasma treatment has been shown to be effective on subcutaneous infections representative of cystic acne. In cases of severe acne, focal treatments of each lesion may not be practical or desirable. Therefore, it is desirable to provide a cold plasma delivery system that can address a large treatment area relevant to both acne and other facial ailments such as those described above.

A system is desired to bathe a large area of complex shape, such as the human face, in a plasma "mask" to reduce the appearance of the acne over the entire face. Disclosed herein is the design for such a plasma mask useful in the treatment of acne as well as complex facial wounds such as those resulting from trauma, melanoma, and other cancers of the face, rosacea, and psoriasis.

An embodiment is described for a cold plasma treatment mask for application to a face having contours, that has a first mask layer and a second mask layer, the first and second mask layers being configured to conform to the contours of the face. A gas inlet and a gas outlet are coupled to a gas containment region between the first and second mask layers, whereby the gas containment region communicatively couples to the gas inlet and gas outlet. An electrical input port is coupled by a plurality of metal tracks to one or more electrical nodes, whereby the one or more electrical nodes having contact with the interior of the gas containment region, wherein the electrical input port is further configured to be coupled to a unipolar high voltage power supply to thereby generate cold plasma in the gas containment region.

Another embodiment is described of a method that forms a first layer of a cold plasma treatment mask, where the first layer is configured to conform to the contours of the face. A second layer is formed adjacent to the first layer, whereby the second layer is configured to form a gas containment region between the first layer and the second layer. A gas inlet and a gas outlet is attached to the second layer, the gas inlet and gas outlet thereby being coupled to the gas containment region, whereby gas can be received from the gas inlet and returned via the gas outlet. An electrical input port is coupled to a plurality of metal tracks to one or more electrical nodes, including the attachment of one or more electrical nodes on an exterior surface of the second layer, and having contact with the interior of the gas containment region, wherein the electrical input port is further configured to be coupled to a unipolar high voltage power supply to thereby generate cold plasma in the internal region. A third layer is formed adjacent to the second layer to provide an external layer to the cold plasma treatment mask.

A further method is described that receives a noble gas mix, or other suitable gas mix. Next, the gas is energized to form a cold plasma within a conformable mask, the conformable mask having a contour conforming to a face of a patient that includes a treatment area, the conformable mask avoiding one or more of an eye socket, a nose and a mouth of the patient. Finally, the cold plasma is maintained within the conformable mask to treat the treatment area.

BRIEF DESCRIPTION OF THE DRAWINGS/FIGURES

FIG. 13 provides a method of using a cold plasma mask application device, according to an embodiment of the present invention.

DETAILED DESCRIPTION OF THE INVENTION

Cold temperature atmospheric pressure plasmas have attracted a great deal of enthusiasm and interest by virtue of their provision of plasmas at relatively low gas temperatures. The provision of a plasma at such a temperature is of interest to a variety of applications, including wound healing, antibacterial processes, various other medical therapies and sterilization.

Cold Plasma Application Device

Figure 1A:
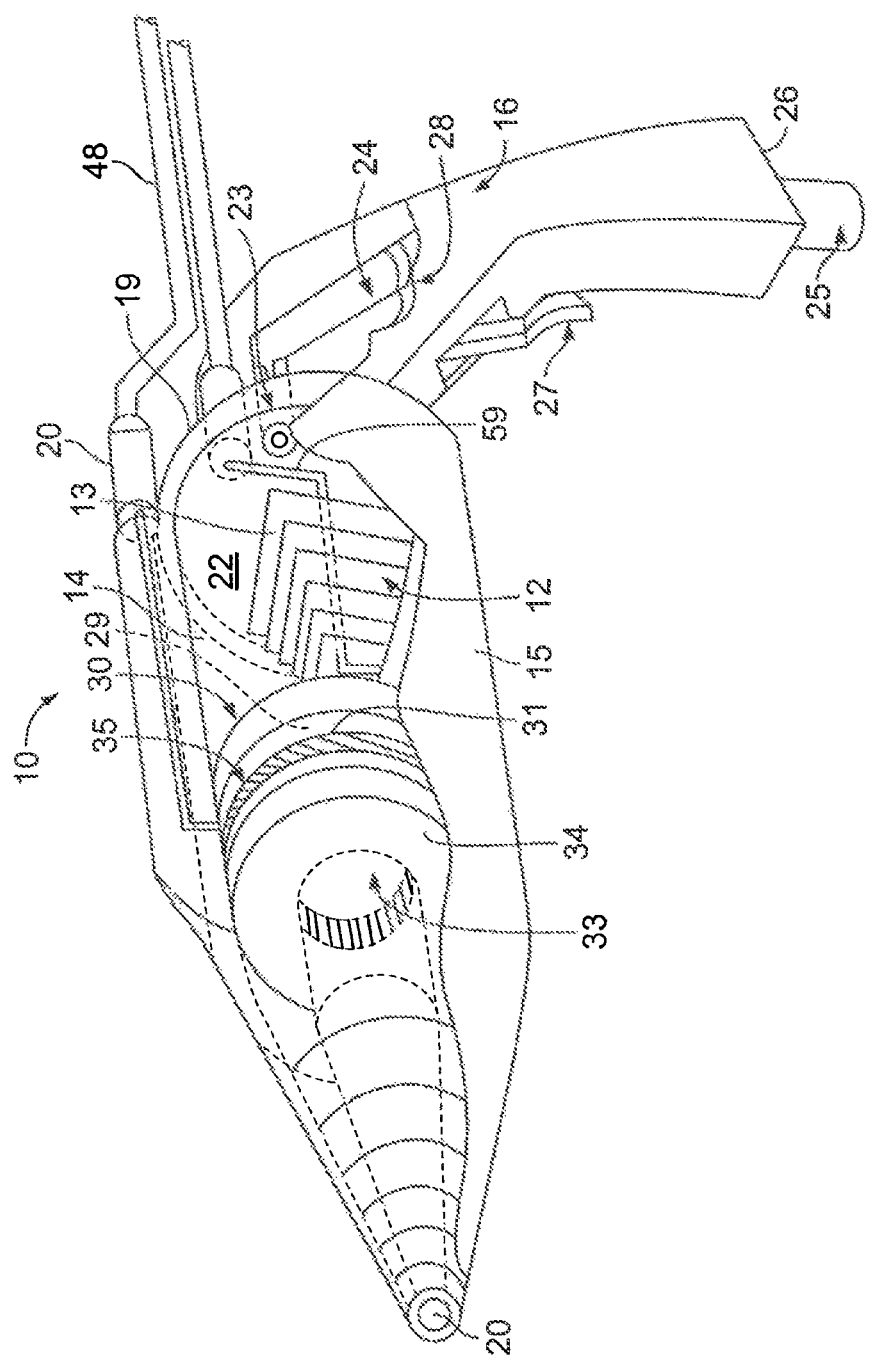
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
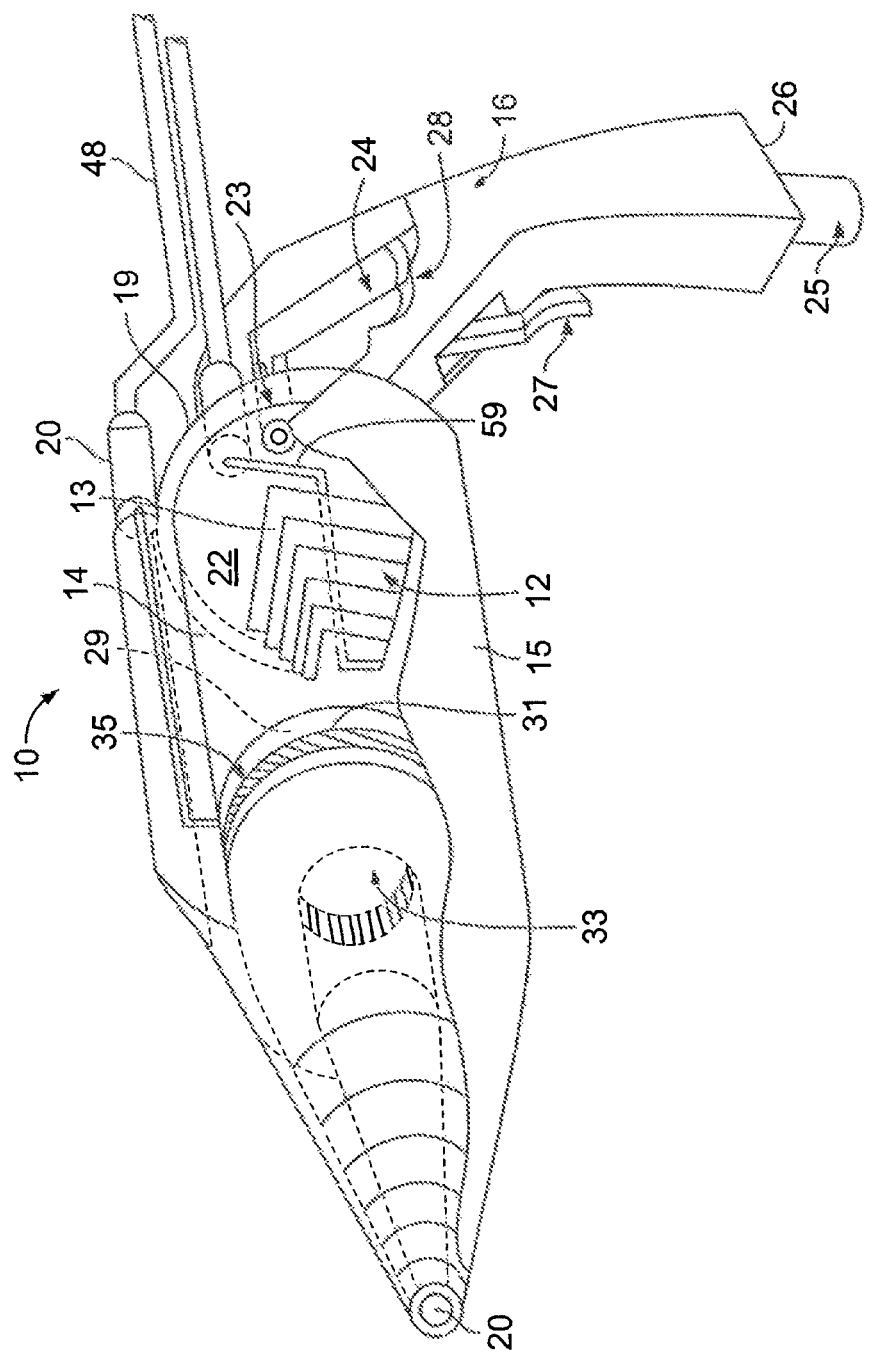
Figure 2A:
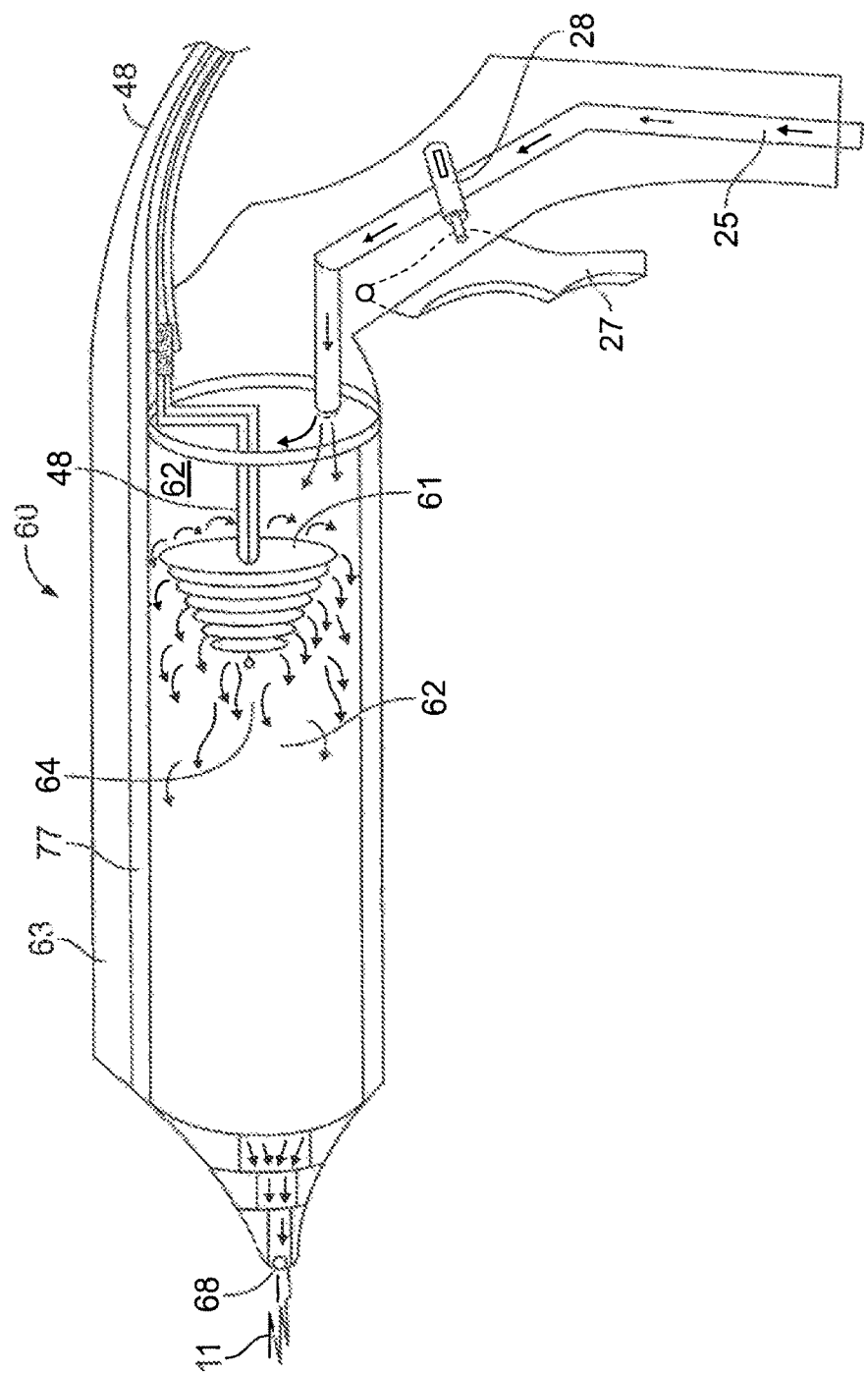
FIGS. 2A and 2B illustrate an embodiment of the cold plasma device without magnets, in accordance with embodiments of the present invention.
Figure 2B:
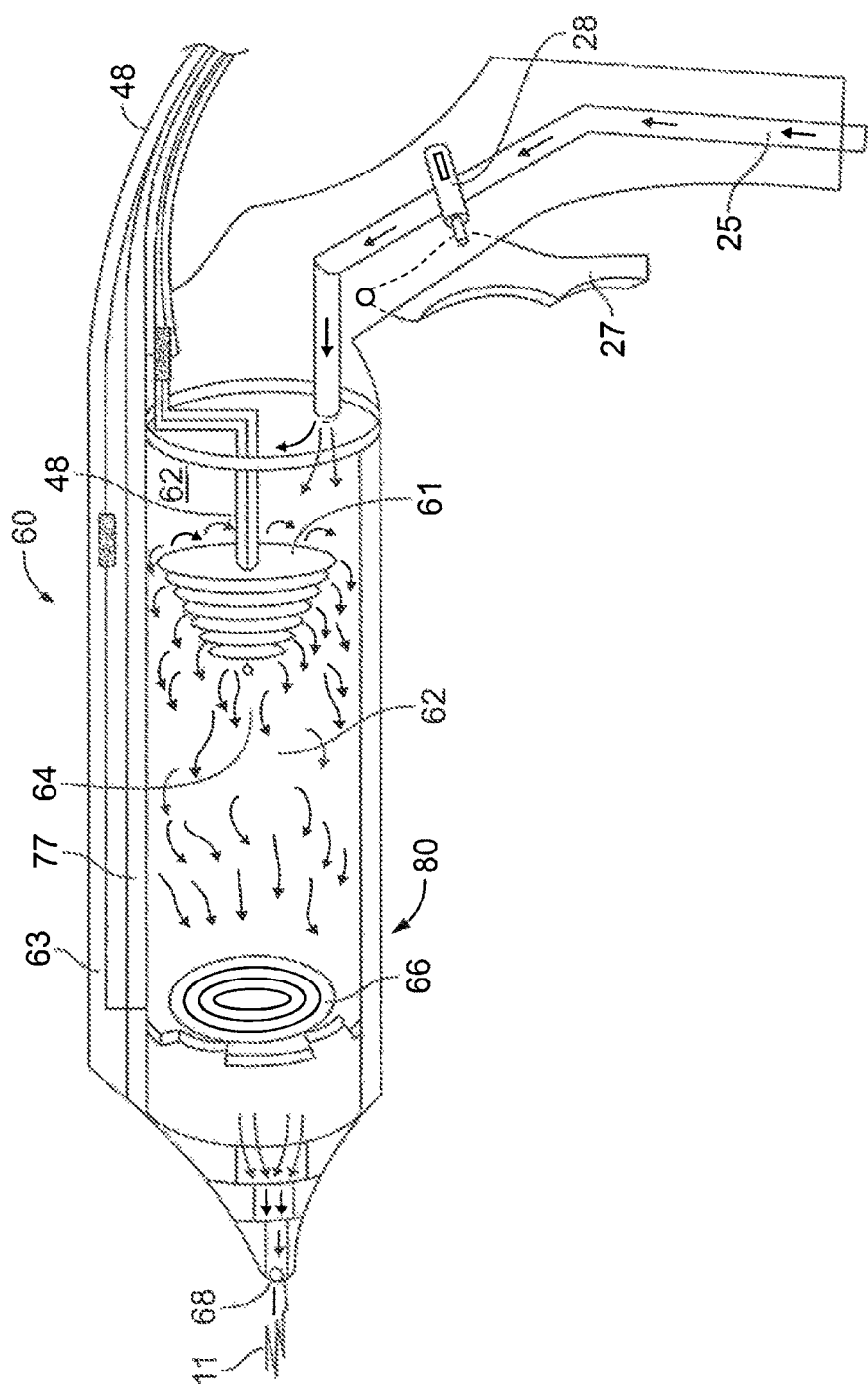

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
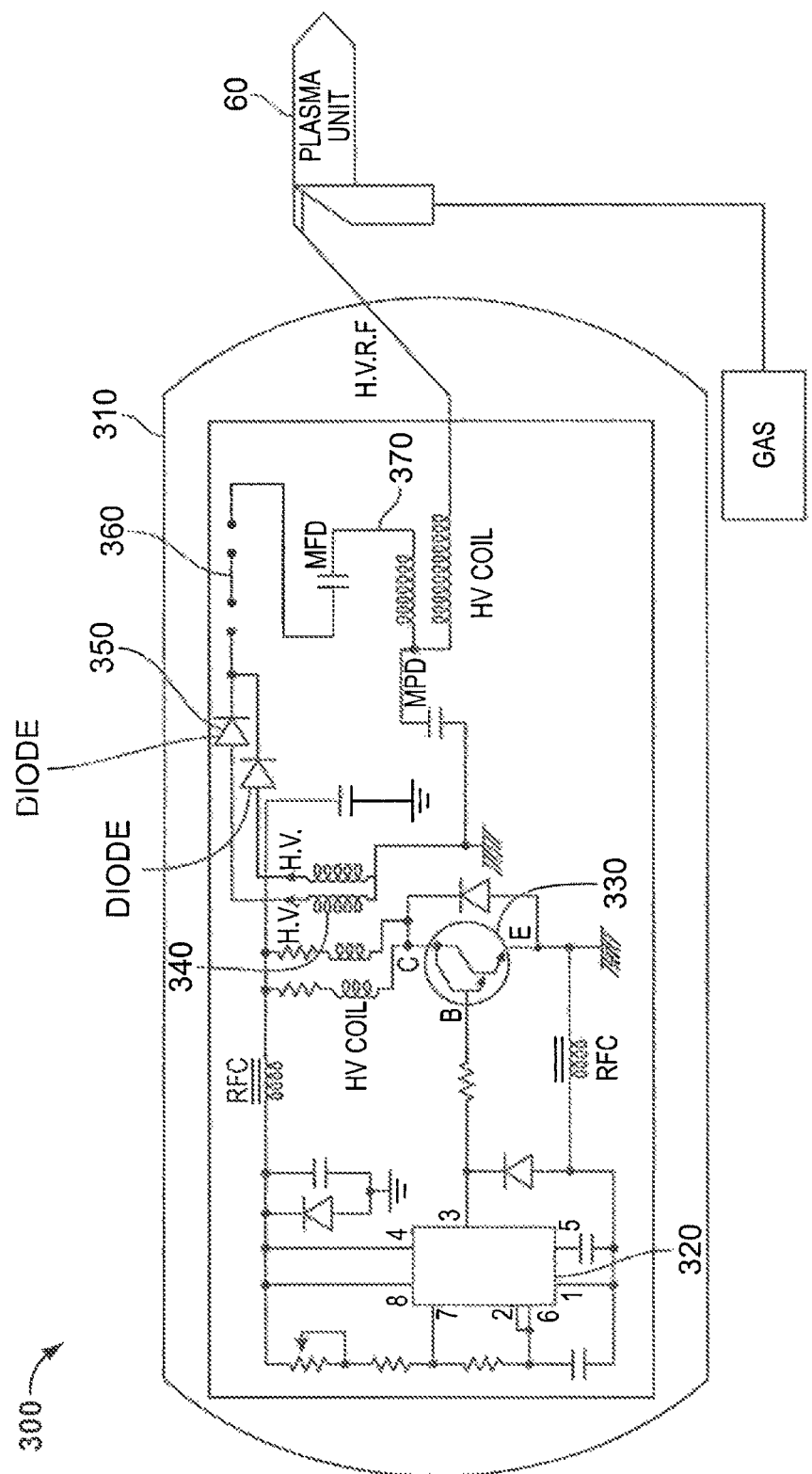
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz—low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz—low MHz range can be generated with an adjustable repetition frequency in the 1 kHz range. The output waveform is shaped similar to the acoustic waveform generated by an impulse such as a bell is struck with a hammer. Here, the impulse is provided when the spark gap (or SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Mask Treatment Device

Figure 4:
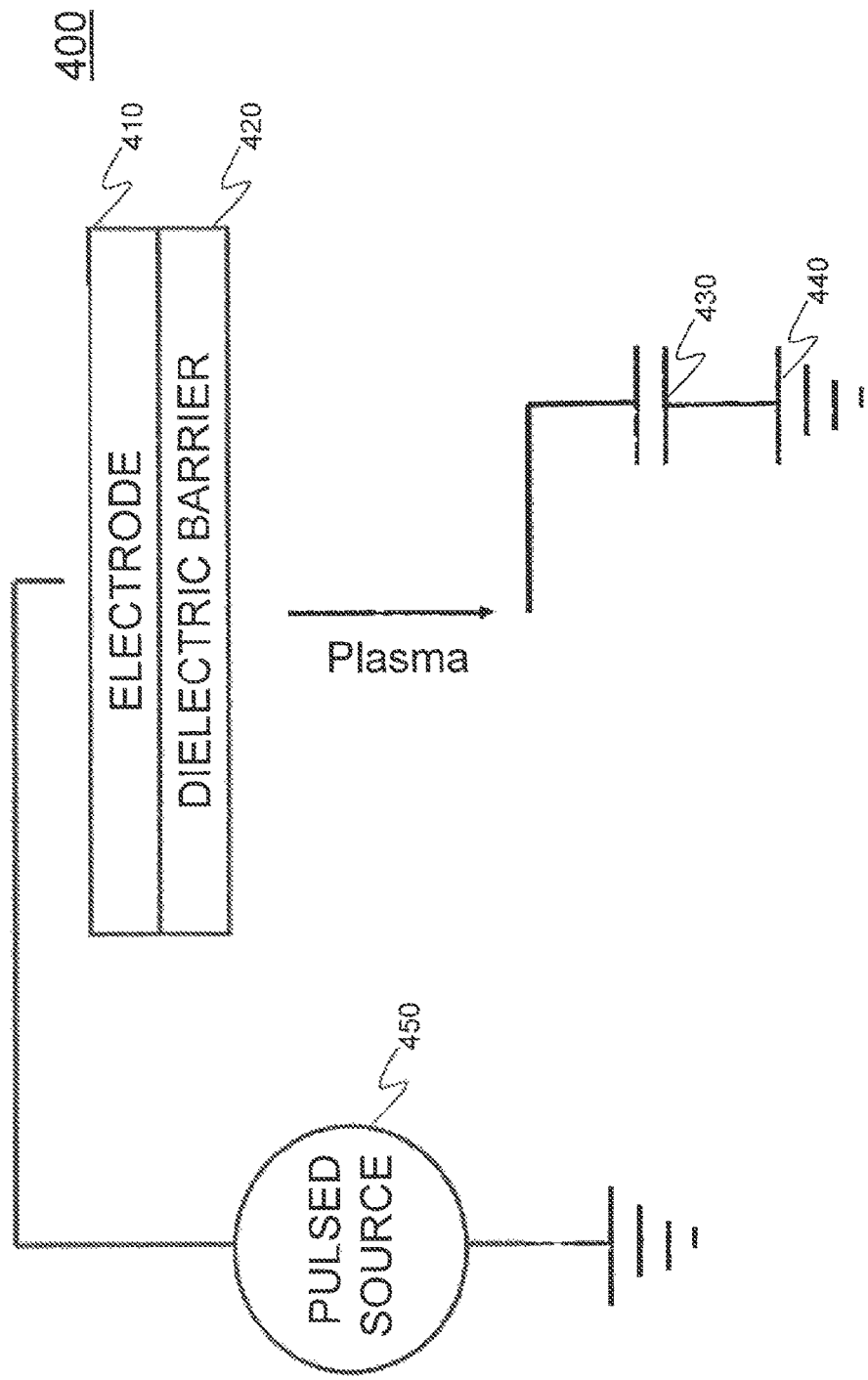
FIG. 4 illustrates the generation of cold plasma resulting from a dielectric barrier device, in accordance with embodiments of the present invention.

Devices, other than the cold plasma device illustrated above in FIG. 1, can also generate cold plasma. For example, cold plasma can also be generated by a dielectric barrier device, which relies on a different process to generate the cold plasma. As FIG. 4 illustrates, a dielectric barrier device (DBD) 400 contains one metal electrode 410 covered by a dielectric layer 420. The electrical return path 430 is formed by the ground 440 that can be provided by the target substrate or the subject undergoing the cold plasma treatment. Energy for the dielectric barrier device 400 can be provided by a power supply 450, such as that described above and illustrated in FIG. 2. More generally, energy is input to the dielectric barrier device in the form of pulsed electrical voltage to form the plasma discharge. By virtue of the dielectric layer, the discharge is separated from the metal electrode and electrode etching is reduced. The chopped DC electrical voltage can be varied in amplitude and frequency to achieve varying regimes of operation.

In exemplary embodiments, the DBD principle is used to provide devices and methods for the application of cold plasma to one or more treatment areas on the face of a patient. The cold plasma application device has a mask form, which provides a confinement dome to which a suitable gas (e.g., helium, oxygen, and the like, including gas combinations) is received, energized to form a cold plasma and provided in close proximity to the desired treatment area, but prevented from reaching unintended areas. Due to the close proximity, the energy of the cold plasma may be buffered in order to provide a lower energy cold plasma. The confinement dome does not cover the eye sockets, nose or mouth—instead, apertures are created in the cold plasma mask application device to allow the eye sockets, nose and mouth to have unimpeded access to the external air. The cold plasma mask application device has support points on the face of the patient to ensure that the confinement dome suitably mirrors the individual contours of the face of the particular patient. The confinement dome can be made using moldable material that prevents penetration by the plasma. Various embodiments of the cold plasma mask application device include an embodiment that allows direct contact of the cold plasma with the treatment area. In an alternative embodiment of the cold plasma mask application device, the cold plasma can be contained in a containment area within the mask, where the containment area is separated from the patient treatment area by a mask layer. In this embodiment, the cold plasma itself acts as a distributed DBD electrode or complex shape, with no direct contact between the cold plasma within the gas confinement area and the treatment area. Instead, it is the electromagnetic fields associated with the cold plasma rather than direct cold plasma contact, provide a therapeutic effect on the treatment area. In further embodiments of the cold plasma mask application device, individualized masks can be manufactured by obtaining a facial scan from which a custom mask can be developed for each patient. Applications to which the various embodiments of the cold plasma mask application device can be applied include the treatment of facial acne, psoriasis, rosacea, facial wounds and skin treatments that benefit from a diminution of skin bacteria.

Figure 5:
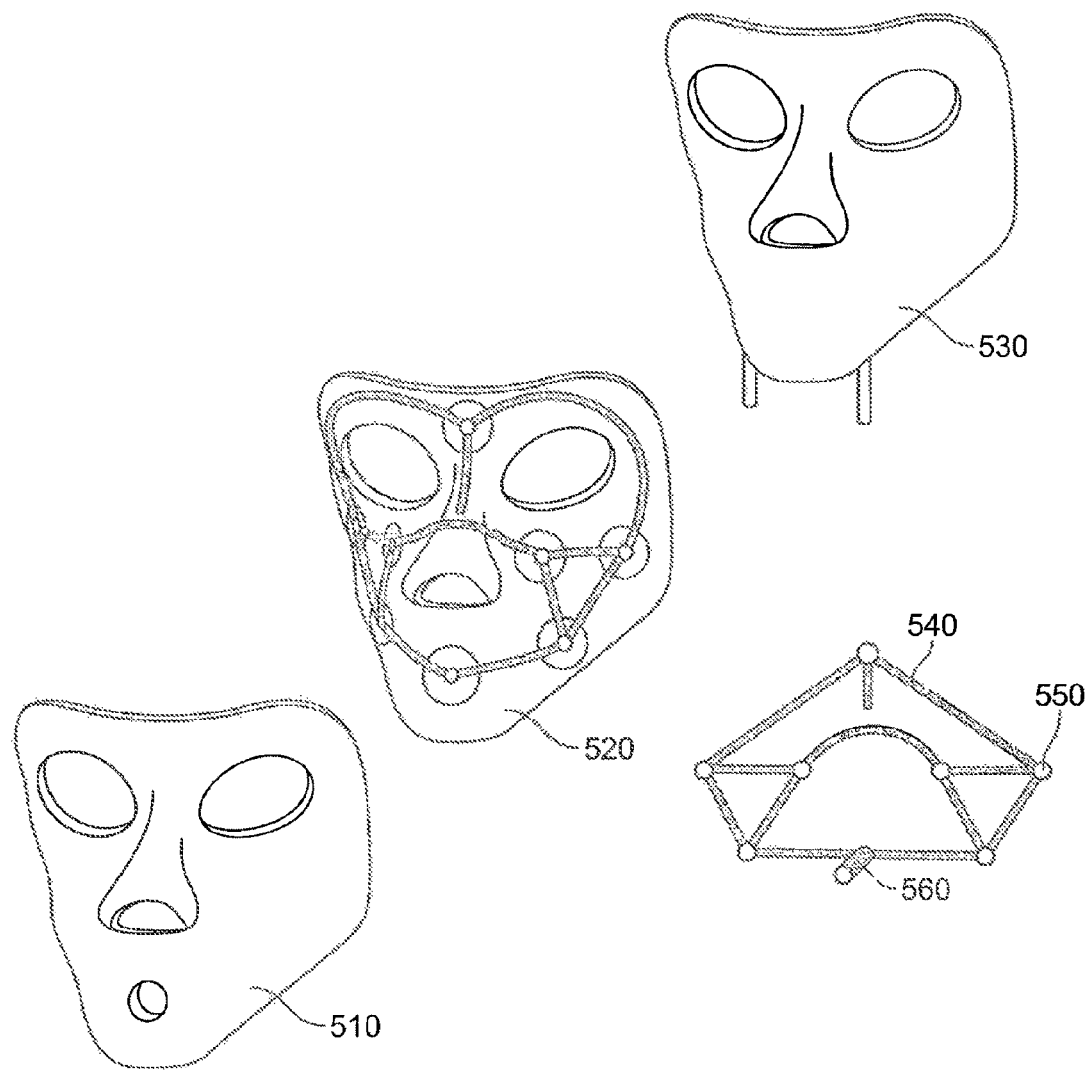
FIG. 5 illustrates a three-layer approach to the formation of a cold plasma mask application device, in accordance with an embodiment of the present invention.

FIG. 5 illustrates one approach to forming the above cold plasma mask application device 500. Cold plasma mask application device 500 is created from three mask layers, 510, 520 and 530 that are sealed together to form the cold plasma mask application device. Inner mask layer 530 is the layer closest to the face of the patient, intermediate mask layer 520 is the intermediate mask layer, and outer mask layer 510 is the outer mask layer farthest from the underlying face of the patient. A metal grid 540 that includes a number of metal electrodes 550 is formed on intermediate mask layer 520, which is described in further detail below. A dielectric covering is provided with each metal electrode 550.

To ensure effective sealing, the three mask layers 510, 520, 530 should fit conformally with one another to facilitate an extremely close relationship fit for the resulting cold plasma treatment mask 500. In an exemplary embodiment, the individual masks are preferably molded to the patient's face in order to ensure that the cold plasma treatment mask provides the proper treatment over a patient face. Such molding can involve the conventional use of moldable materials, together with an appropriate molding process that begins with an exact face mold of the patient and finishes with a mask that snugly fits the contours of the face of the patient while providing the means for accepting electrical and gas inputs to form the cold plasma in close proximity to the face of the patient.

In an exemplary molding embodiment, the molding process generates the three mask layers 510, 520, 530 from the same face mold to ensure the required close fitting relationship. Between the inner mask layer 530 and the intermediate mask layer 520, a gas containment region (not shown in FIG. 5) is formed into which helium or any other suitable gas, including gas mixtures, is introduced. By virtue of the contact of the metal grid electrodes 550 with the gas, a cold plasma is formed in the gas containment region.

Figure 6:
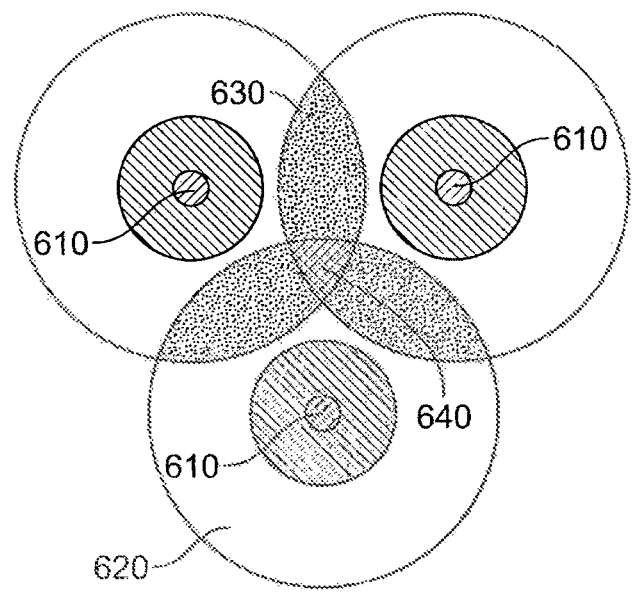
FIG. 6 illustrates an exemplary configuration of electrical pod electrodes and the resulting cold plasma active regions, in accordance with an embodiment of the present invention.

FIG. 6 illustrates the underlying principle of metal grid 540. As already illustrated in FIG. 5, metal grid 540 consists of one or more gold-plated nickel pod electrodes that are connected by metal tracks to an input electrode 560. The input electrode receives the input high voltage power supply signal of the type that can be obtained from, for example, pulse source 450 in FIG. 4, or the source illustrated in FIG. 3. Referring to FIG. 6, each pod electrode 610 results in the creation of cold plasma active regions 620 beneath the pod electrode 610, whose intensity diminishes with increasing distance away from the pod electrode 610. By arranging the electrodes 610 in close proximity, the cold plasma active regions 620 can overlap. For example, area 630 is a doubly active region. Similarly, area 640 is a triply active region.

As noted above, the electrodes 610 ionize the gas (e.g., helium) contained in the gas containment region formed between the inner mask layer 530 and the intermediate mask layer 520 of the mask assembly. The ionized gas (e.g., ionized helium) then acts as an electrode similar to electrode 410 in FIG. 4. The ionized gas electrode evenly covers the distal surface (i.e., furthest from the patient face) of the inner mask layer 530. This creates a dielectric barrier device (DBD) plasma effect between the proximal surface of inner mask layer 530 and the patient face. The use of an ionized gas as the DBD electrode to achieve an even distribution that is conformal to the treatment area is a significant advancement in the field of cold plasma devices. In such an embodiment, the gas (e.g., helium) does not contact the patient face. Rather, the ionized gas acts as a "distributed electrode" and ensures a uniform application of the DBD plasma induced effects.

In an alternate embodiment, the ionized gas can be allowed to contact the patient face. In such an embodiment, one or more apertures in the inner mask layer 530 can be formed to allow a portion of the gas to exit and make contact with the patient's face. The position of the apertures would be located to be consistent with the treatment area(s) of interest.

Figure 7:
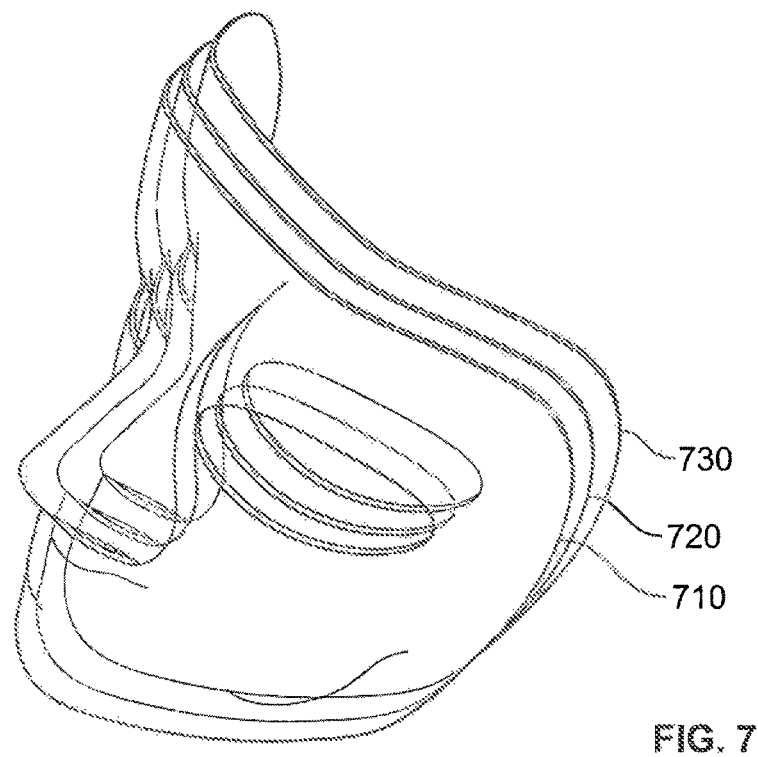
FIG. 7 illustrates an exemplary set of three mask layers for a cold plasma mask application device, in accordance with an embodiment of the present invention.

FIG. 7 illustrates a plasma mask having a three-layer construction, with the three mask layers 710, 720, 730 shown prior to assembly. In this embodiment, the mask layers 710, 720, 730 use clear acrylic material. In a particular embodiment, the mask layers can use 1.75 mm thick clear acrylic material.

As noted above, inner mask layer 730 is the layer that is most proximal to the face. Inner mask layer 730 can closely match the contours of the patient's face. In one embodiment, the "close match" can be achieved with a variety of data capture and mask construction methods. To acquire the shape of a patient face, a variety of digital and mechanical methods are available including but not limited to surface laser scanning, stereophotogrammetry, and direct molding with a curable material. To create inner mask layer 730, a replica of the face may be generated by casting from a mold, vacuum or heat forming to a mold, or a myriad of rapid prototyping techniques from three-dimensional digital data. The other two mask layers, intermediate mask layer 720 and external mask layer 710, are formed using the same approach as that used for inner mask layer 730. Other approaches that yield mask layers that are conformal to the patient's face are equally applicable, and within the scope of the present invention.

Figure 8:
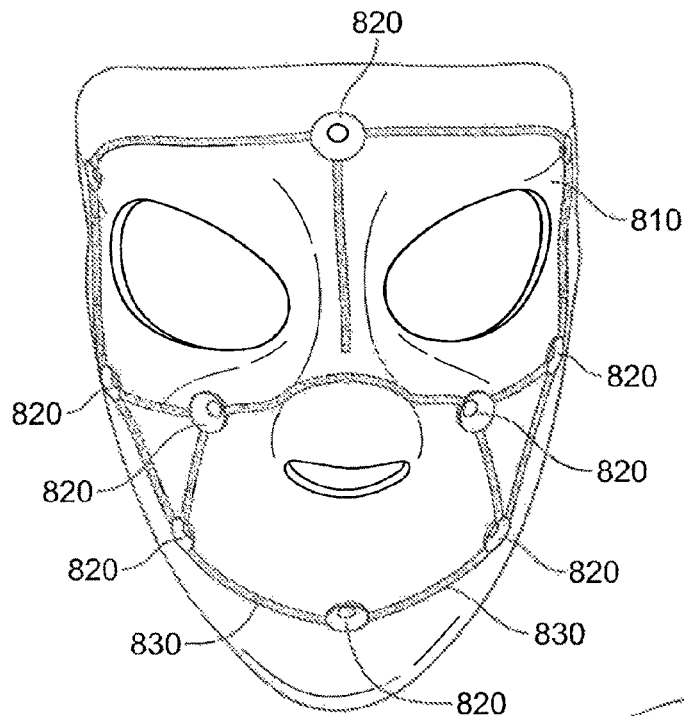
FIG. 8 illustrates an exemplary placement of the electrical grid on the intermediate mask layer, in accordance with an embodiment of the present invention.

FIG. 8 illustrates the fitting of the nickel pod electrodes 820 on the intermediate mask layer 810. Tracks 830 are used to electrically connect the nickel pod electrodes 820 to each other, and to the electrical input electrode (not shown). The nickel pod electrodes 820 use nickel contacts placed on a dielectric plug having a thickness approximately the same as that of the intermediate mask layer 810. The diameter of the dielectric plug matches the aperture diameters formed in the intermediate mask layer 810. In an embodiment of the present invention, dielectric plugs can be manufactured using clear quartz.

Figure 9:
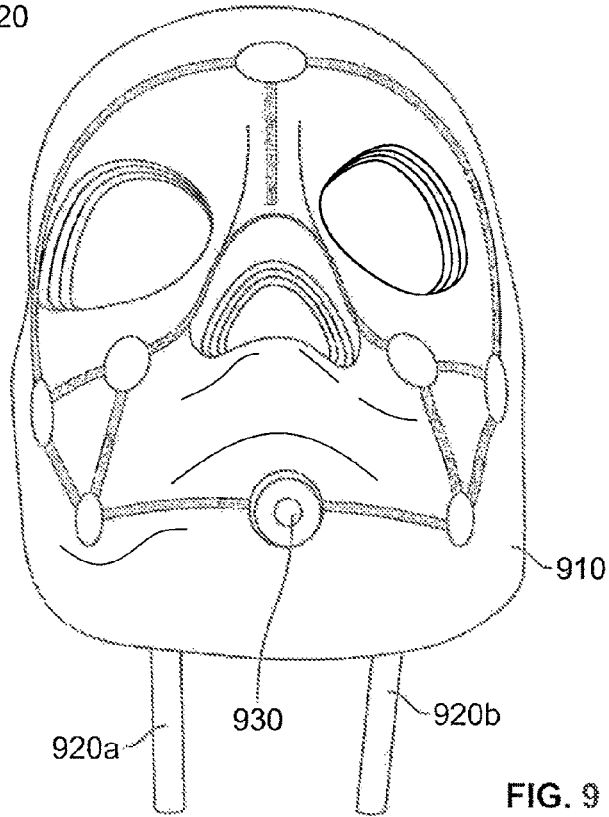
FIG. 9 illustrates a prototype of a cold plasma mask application device that shows the gas inlet and gas outlet, and electrical input node, in accordance with an embodiment of the present invention.

FIG. 9 illustrates an approach to providing a gas inlet and gas outlet for provision of gas to the gas containment region between inner mask layer and intermediate mask layer. FIG. 9 shows outer mask layer 910 that has already been formed over intermediate mask layer, and underlying inner mask layer. In an exemplary embodiment, helium gas, a noble gas or other suitable gas would be supplied via gas inlet 920a and returned via gas outlet 920b. In an embodiment, gas inlet 920a and gas outlet 920b can be formed using materials such as polypropylene, polyethylene, or PTFE. In an additional embodiment, the gas can be recirculated through a pump in order to improve the gas usage efficiency. FIG. 9 also shows electrical input electrode 930 is shown to which electrical energy from a pulse source would be applied, as noted above. In a still further embodiment, the gas can be recirculated by convection, and thereby improve the gas usage efficiency.

Figure 10:
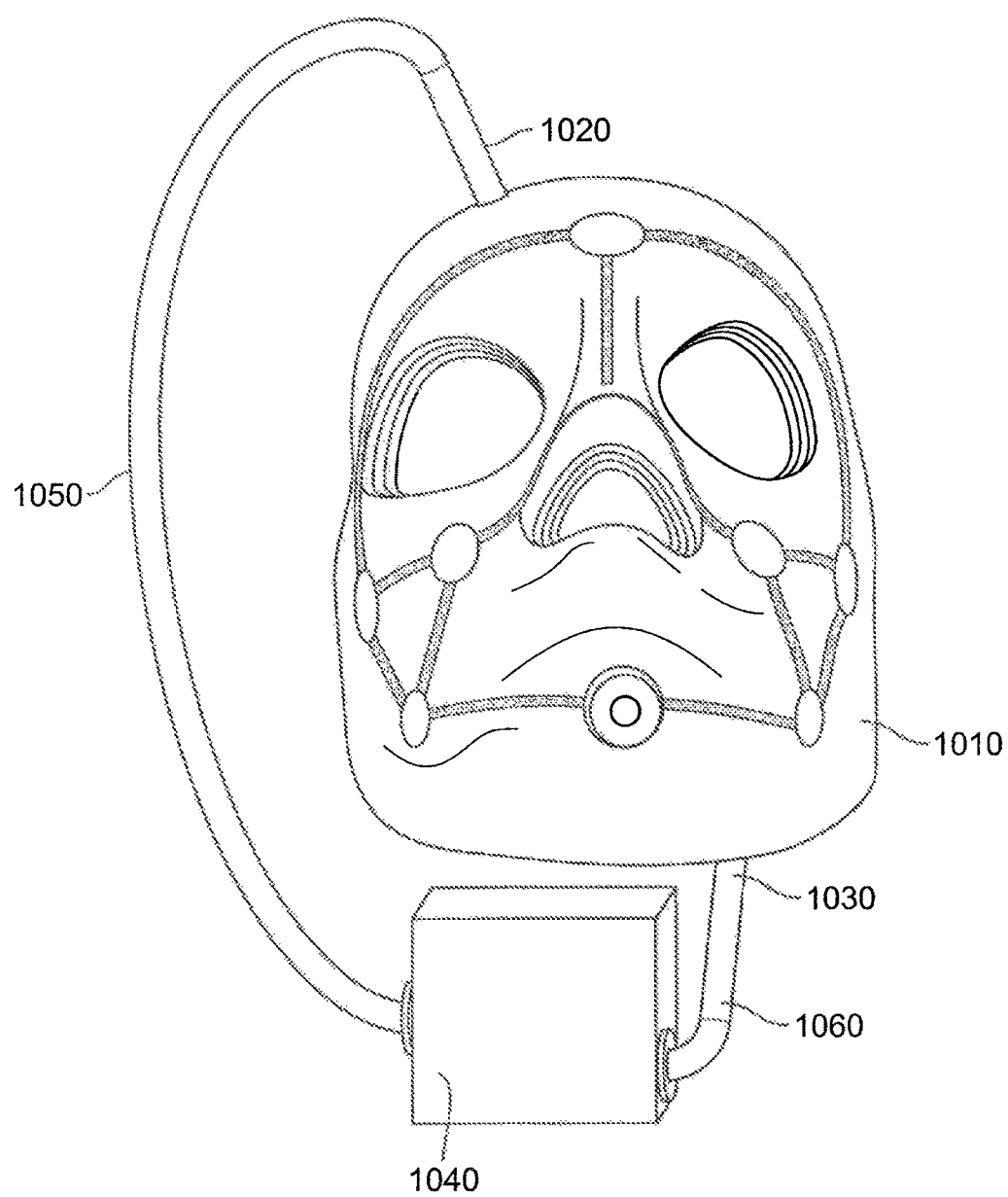
FIG. 10 illustrates a cold plasma mask application device that uses gas recirculation, in accordance with an embodiment of the present invention.

FIG. 10 illustrates an approach to providing recirculation of gas to a sealed gas containment region. Such an embodiment avoids the problem of overheating in the use of a sealed gas containment region. FIG. 10 shows cold plasma mask 1010 with a gas outlet 1020 from and a gas inlet 1030 from the gas containment region. Energized gas would exit from gas outlet 1020 and flow into chamber 1040 via pipe 1050. Chamber 1040 provides for the quenching of the energized gas. Following quenching, gas returns via pipe 1060 to gas inlet 1030. In another embodiment, chamber 1040 can also provide for additional gas storage. Note that although gas pipes 1050, 1060 and gas outlet 1020, gas inlet 1030 and chamber 1040 are shown as separated from cold plasma mask 1010, any one or more of these items can be integrated within the cold plasma mask 1010. In a further approach to the overheating issue, the cold plasma mask can be run for short durations using an appropriate on/off cycle.

Cold Plasma Mask Manufacturing and Usage Method

Figure 11:
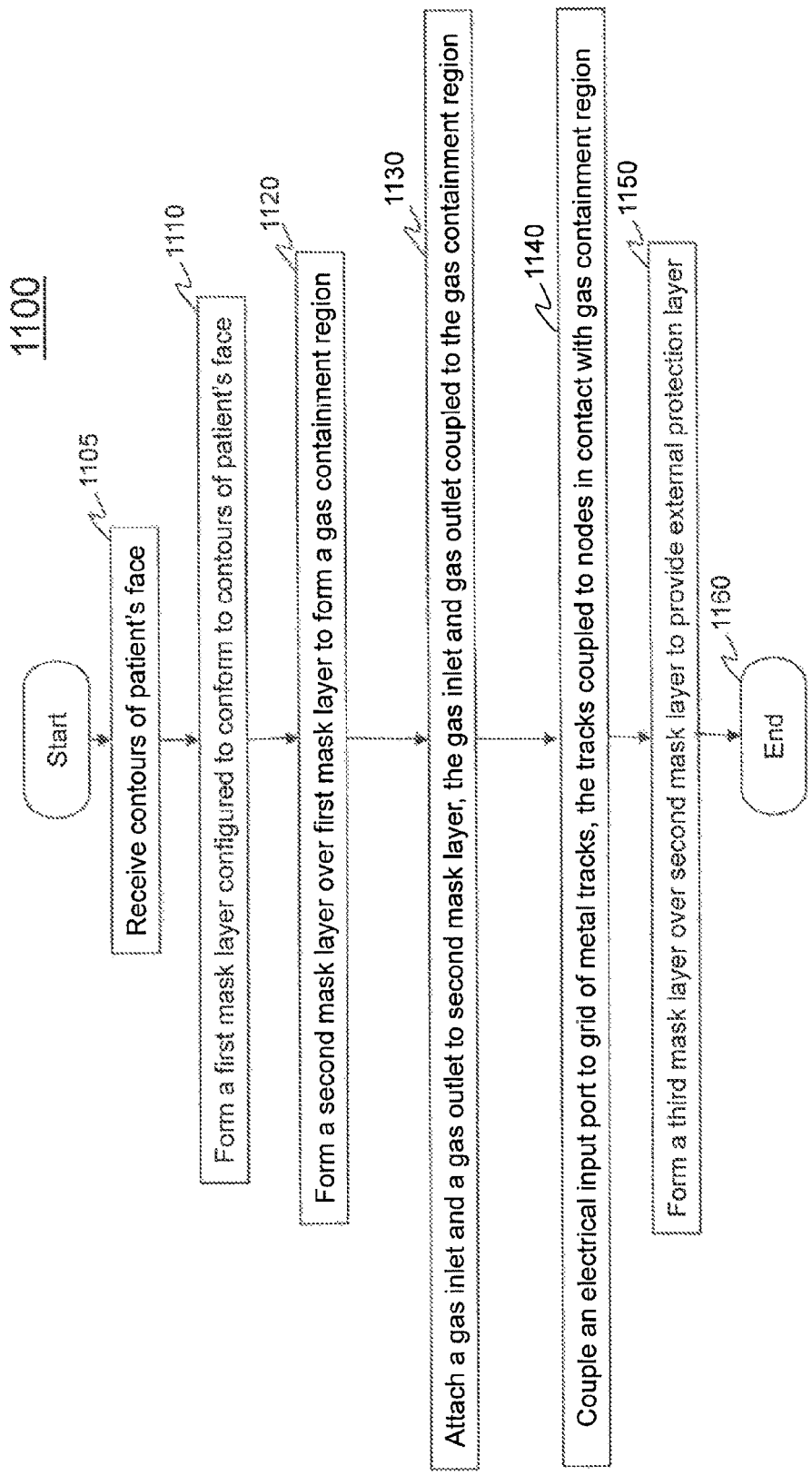
FIG. 11 illustrates a method of forming a cold plasma using a cold plasma mask application device, in accordance with an embodiment of the present invention.

FIG. 11 provides a flowchart of an exemplary method 1100 to provide manufacture a cold plasma mask treatment device, according to an embodiment of the present invention.

The process begins at step 1110. In step 1110, a first mask layer of a cold plasma mask application device is formed, the first mask layer being configured to conform to the contours of the face. In an embodiment, a first mask layer 530 is formed. In some embodiments of this method, an acquisition of the face contours precedes step 1110.

In step 1120, a second mask layer is formed over the first mask layer, the second mask layer configured to form a gas containment region between the first layer and the second layer. In an embodiment, a second mask layer 520 is formed to form a gas containment region between second mask layer 520 and first mask layer 530.

In step 1130, a gas inlet and a gas outlet is attached to the second layer, the gas inlet and gas outlet thereby being coupled to the gas containment region, whereby gas can be received from the gas inlet and returned via the gas outlet. In an embodiment, gas inlet 920a and gas outlet 920b is formed to be communicatively coupled to the gas containment region.

In step 1140, an electrical input port is coupled by a plurality of metal tracks to one or more electrical nodes in an electrical grid, the one or more electrical nodes formed on an exterior surface of the second layer, and having contact with the interior of the internal region, wherein the electrical port is further configured to be coupled to a unipolar high voltage power supply to thereby generate cold plasma in the internal region.

In step 1150, a third mask layer is formed over the second mask layer to provide an external protection layer to the cold plasma mask application device.

At step 1160, method 1100 ends.

Figure 12:
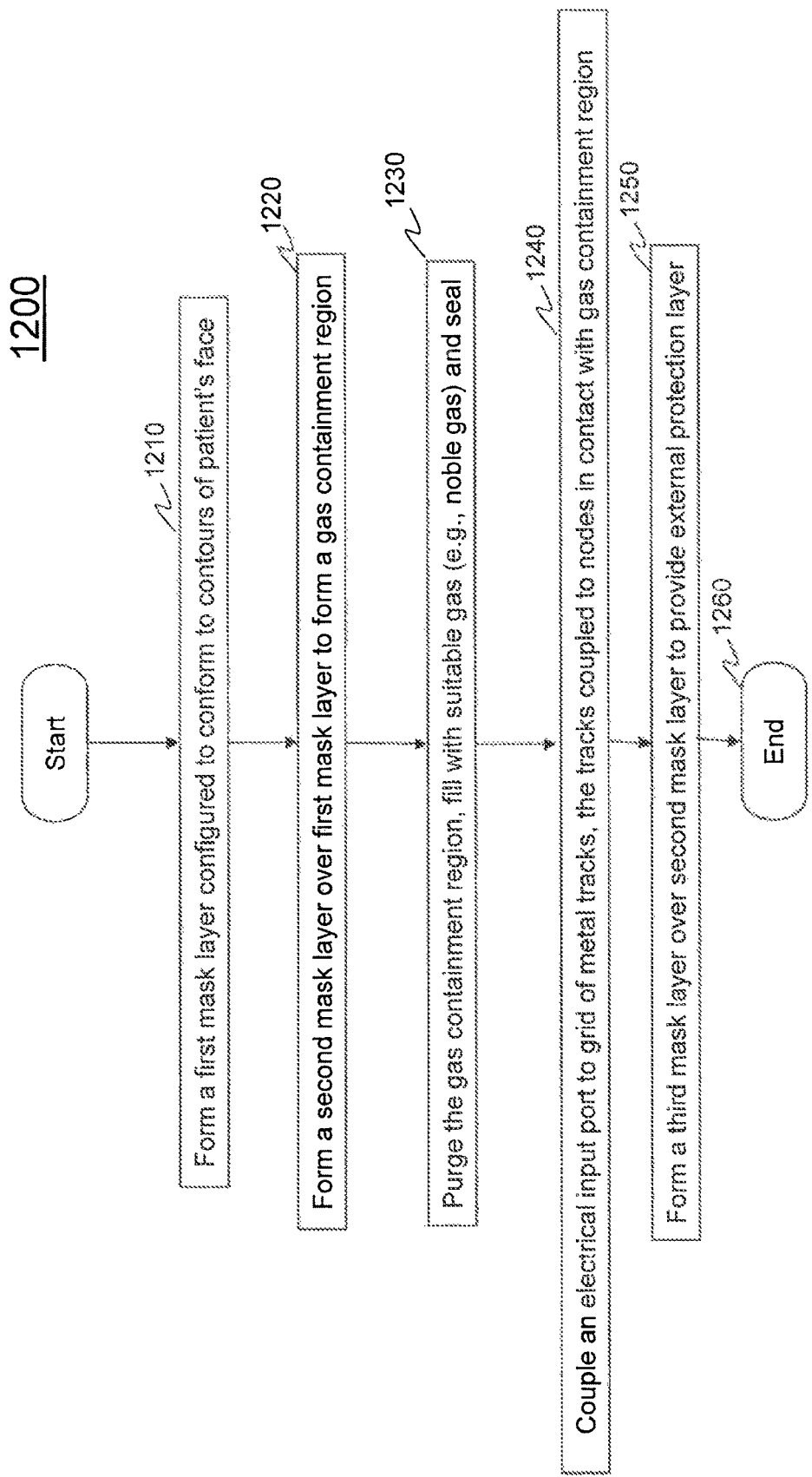
FIG. 12 illustrates a further method of forming a cold plasma using a cold plasma mask application device, in accordance with an embodiment of the present invention.

FIG. 12 provides a flowchart of an exemplary method 1200 to provide manufacture a cold plasma mask treatment device, according to an embodiment of the present invention.

The process begins at step 1205. In step 1205, contours of a face are received.

In step 1210, a first mask layer of a cold plasma mask application device is formed, the first mask layer being configured to conform to the contours of the face. In an embodiment, a first mask layer 530 is formed.

In step 1220, a second mask layer is formed over the first mask layer, the second mask layer configured to form a gas containment region between the first layer and the second layer. In an embodiment, a second mask layer 520 is formed to form a gas containment region between second mask layer 520 and first mask layer 530.

In step 1230, the gas containment region is purged, filled with suitable gas (such as a noble gas), and the gas containment region is sealed.

In step 1240, an electrical input port is coupled by a plurality of metal tracks to one or more electrical nodes in an electrical grid, the one or more electrical nodes formed on an exterior surface of the second layer, and having contact with the interior of the internal region, wherein the electrical port is further configured to be coupled to a unipolar high voltage power supply to thereby generate cold plasma in the internal region.

In step 1250, a third mask layer is formed over the second mask layer to provide an external protection layer to the cold plasma mask application device.

At step 1260, method 1200 ends.

FIG. 13 provides a flowchart of an exemplary method 1300 to use a cold plasma mask application device, according to an embodiment of the present invention.

The process begins at step 1310. In step 1310, a suitable gas is received.

In step 1320, the gas is energized to form a cold plasma within a conformable mask, the conformable mask having a contour conforming to a face of a patient that includes a treatment area, the conformable mask avoiding one or more of an eye socket, a nose and a mouth of the patient.

In step 1330, the cold plasma is maintained within the conformable mask to treat the treatment area.

At step 1340, method 1300 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma treatment mask for application to a face having contours, comprising:
  a first mask layer and a second mask layer, the first and second mask layers being configured to conform to the contours of the face;
  a gas inlet and a gas outlet coupled to a gas containment region between the first and second mask layers, the gas containment region communicatively coupled to the gas inlet and gas outlet; and
  an electrical input port coupled by a plurality of metal tracks to one or more electrical nodes, the one or more electrical nodes having contact with an interior of the gas containment region, wherein the electrical input port is further configured to be coupled to a unipolar high voltage power supply to thereby generate cold plasma in the gas containment region.

2. The cold plasma treatment mask of claim 1, further comprising:
one or more cutouts in the cold plasma treatment mask in positions associated with at least one of a mouth, a nose and an eye of the face.

3. The cold plasma treatment mask of claim 1, wherein gas can be received from the gas inlet and returned via the gas outlet, and wherein the gas comprises helium.

4. The cold plasma treatment mask of claim 1, wherein locations of the one more electrical nodes are aligned with treatment areas of the face.

5. A cold plasma treatment mask for application to a face having contours, comprising:
a first layer configured to conform to the contours of the face;
a second layer adjacent to the first layer, and configured to form a gas containment region between the first layer and the second layer;
a gas inlet and a gas outlet coupled to the gas containment region, whereby gas can be received from the gas inlet and returned via the gas outlet;
an electrical input port coupled by a plurality of metal tracks to one or more electrical nodes, the one or more electrical nodes formed on an exterior surface of the second layer, and having contact with an interior of the gas containment region, wherein the electrical port is further configured to be coupled to a unipolar high voltage power supply to thereby generate cold plasma in the gas containment region; and
forming a third layer adjacent to the second layer to provide an external layer to the cold plasma treatment mask.

6. The cold plasma treatment mask of claim 5, further comprising:
one or more cutouts in the mask in positions associated with at least one of a mouth, a nose and an eye of the face.

7. The cold plasma treatment mask of claim 5, wherein the gas comprises helium.

8. The cold plasma treatment mask of claim 5, wherein locations of the one or more electrical nodes are aligned with treatment areas of the face.

9. The cold plasma treatment mask of claim 5, wherein the first layer, the second layer and third layer comprise acrylic.

10. The cold plasma treatment mask of claim 5, wherein the one or more electrical nodes comprise gold-plated nickel formed on quartz plugs.

11. The cold plasma treatment mask of claim 5, wherein the one or more electrical nodes include two electrical nodes in sufficient proximity to create double-active cold plasma regions.

12. The cold plasma treatment mask of claim 5, wherein the one or more electrical nodes include three electrical, nodes in sufficient proximity to create triple-active cold plasma regions.

13. A method comprising:
forming a first layer of a cold plasma treatment mask, the first layer being configured to conform to contours of a face;
forming a second layer adjacent to the first layer, the second layer configured to form a gas containment region between the first layer and the second layer;
attaching a gas inlet and a gas outlet to the second layer, the gas inlet and gas outlet thereby being coupled to the gas containment region, whereby gas can be received from the gas inlet and returned via the gas outlet;
attaching an electrical input port coupled by a plurality of metal tracks to one or more electrical nodes, the attaching further including forming the one or more electrical nodes on an exterior surface of the second layer, and having contact with an interior of the gas containment region wherein the electrical input port is further configured to be coupled to a unipolar high voltage power supply to thereby generate cold plasma in the internal region; and
forming a third layer adjacent to the second layer to provide an external layer to the cold plasma treatment mask.

14. The method of claim 13, wherein the first layer, the second layer and the third layer comprise acrylic.

15. The method of claim 13, wherein the one or more electrical nodes comprise gold-plated nickel formed on quartz plugs.

16. The method of claim 13, wherein the forming the one or more electrical nodes includes forming two electrical nodes in sufficient proximity to create double-active cold plasma regions.

17. The method of claim 13, wherein the forming the one or more electrical nodes includes forming three electrical nodes in sufficient proximity to create triple-active cold plasma regions.

18. A cold plasma treatment device comprising:
a cold plasma generation device configured to receive a gas, and to generate a cold plasma by energizing the gas; and
a mask conformable to a face of a patient, the face having a desired treatment area, the mask having a contour to avoid one or more of an eye socket, a nose and a mouth of the patient, the contour configured to maintain the cold plasma in an area that includes the desired treatment area.

19. A method comprising:
receiving a gas;
energizing the gas to form a cold plasma within a conformable mask, the conformable mask having a contour conforming to a face of a patient that includes a treatment area, the conformable mask avoiding one or more of an eye socket, a nose and a mouth of the patient; and
maintaining the cold plasma within the conformable mask to treat the treatment area.

20. The method of claim 19, further comprising:
applying the cold plasma to the treatment area as part of a treatment of one or more of facial acne, psoriasis, facial wounds and skin treatments that benefit from a diminution of skin bacteria.

21. A method comprising:
forming a first layer of a cold plasma treatment mask, the first layer being configured to conform to contours of a face;
forming a second layer adjacent to the first layer, the second layer configured to form a gas containment region between the first layer and the second layer;
purging the gas containment region, filling the gas containment region with a gas, and sealing the gas containment region;
attaching an electrical input port coupled by a plurality of metal tracks to one or more electrical nodes, the attaching further including forming the one or more electrical nodes on an exterior surface of the second layer, and having contact with an interior of the gas containment region, wherein the electrical input port is further configured to be coupled to a unipolar high voltage power supply to thereby generate cold plasma in the internal region; and forming a third layer adjacent to the second layer to provide an external layer to the cold plasma treatment mask.

22. A method comprising:

forming a first layer of a cold plasma treatment mask, the first layer being configured to conform to contours of a face;

forming a second layer adjacent to the first layer, the second layer configured to form a gas containment region between the first layer and the second layer;

attaching a gas recirculation system to the gas containment region, the gas recirculation system coupled to a gas outlet and a gas inlet of the gas containment region to thereby recirculate gas;

attaching an electrical input port coupled by a plurality of metal tracks to one or more electrical nodes, the attaching further including forming the one or more electrical nodes on an exterior surface of the second layer, and having contact with an interior of the gas containment region, wherein the electrical input port is further configured to be coupled to a unipolar high voltage power supply to thereby generate cold plasma in the internal region; and forming a third layer adjacent to the second layer to provide an external layer to the cold plasma treatment mask.

\* \* \* \* \*